US00PP20468P2

(12) United States Plant Patent
Quesada

(10) Patent No.: US PP20,468 P2
(45) Date of Patent: Nov. 10, 2009

(54) ***DRACAENA* PLANT NAMED 'SONG OF LA TIGRA'**

(50) Latin Name: *Dracaena reflexa lam.*
Varietal Denomination: Song of La Tigra

(75) Inventor: Eliseo Cambronero Quesada, Los Cerritos (CR)

(73) Assignees: A. C. Alderden, Mijdrecht (NL); R. de Leeuw, Mijdrecht (NL)

( * ) Notice: Subject to any disclaimer, the term of this patent is extended or adjusted under 35 U.S.C. 154(b) by 65 days.

(21) Appl. No.: 11/983,686

(22) Filed: Nov. 10, 2007

(51) Int. Cl.
*A01H 5/00* (2006.01)

(52) U.S. Cl. ..... Plt./383
(58) Field of Classification Search ..... Plt./383
See application file for complete search history.

(56) References Cited

OTHER PUBLICATIONS

UPOV-ROM GTITM, Plant Variety Database, 2008/05, GTI Jouve Retrieval Software, citation for 'Song of La Tigra'.*

* cited by examiner

*Primary Examiner*—Annette H. Para
*Assistant Examiner*—Susan B McCormick Ewoldt
(74) *Attorney, Agent, or Firm*—Mark P. Bourgeois

(57) ABSTRACT

A new cultivar of *Dracaena* plant named 'Song of La Tigra' that is characterized by small dark green leaves, a compact habit and short internodes.

1 Drawing Sheet

Botanical classification: *Dracaena reflexa lam.*
Variety denomination: 'Song of La Tigra'.

BACKGROUND OF THE INVENTION

The present invention relates to a new and distinct cultivar of *Dracaena* plant botanically known as *Dracaena reflexa lam.* and hereinafter referred to by the cultivar name 'Song of La Tigra'.

The new cultivar was discovered in 2001 in an outdoor nursery in a cultivated area of Rio Quarto, Costa Rica. 'Song of La Tigra' was discovered as a naturally occurring branch mutation of an unnamed cultivar of *Dracaena reflexa lam.* (not patented).

Asexual reproduction by terminal cuttings of the new cultivar 'Song of La Tigra' was first taken in 2001 in Rio Quarto, Costa Rica.

Since that time, under careful observation, the unique characteristics of the new cultivar have been uniform, stable and reproduced true to type in successive generations of asexual reproduction.

SUMMARY OF THE INVENTION

The following represent the distinguishing characteristics of the new *Dracaena* cultivar 'Song of La Tigra'. These traits in combination distinguish 'Song of La Tigra' as a new and distinct cultivar.

1. *Dracaena* 'Song of La Tigra' exhibits small dark green leaves.
2. *Dracaena* 'Song of La Tigra' exhibits a compact habit.
3. *Dracaena* 'Song of La Tigra' exhibits short internodes.

The closest comparison cultivar is the parent plant an unnamed cultivar of *Dracaena reflexa lam.* 'Song of La Tigra' is distinguishable from the parent plant by the following characteristics:

1. 'Song of La Tigra' has smaller leaves.
2. 'Song of La Tigra' has shorter internodes.

'Song of La Tigra' is distinguishable from typical plants of the species *Dracaena reflexa lam.* by the following characteristics:

1. 'Song of La Tigra' has smaller leaves.
2. 'Song of La Tigra' has shorter internodes.
3. 'Song of La Tigra' has stronger stems.

BRIEF DESCRIPTION OF THE DRAWING

The accompanying photograph illustrates the distinguishing traits of *Dracaena* 'Song of La Tigra'. The plant in the photograph shows an overall view of a 7 month old plant. The photograph was taken using conventional techniques and although colors may appear different from actual colors due to light reflectance, it is as accurate as possible by conventional photographic techniques.

BOTANICAL DESCRIPTION OF THE PLANT

The following is a detailed description of the new *Dracaena* cultivar named 'Song of La Tigra'. Data was collected in Boskoop, The Netherlands from plants grown in Honselersdijk, The Netherlands. The time of year was winter. The plants were 7 month old greenhouse grown plants in 15 cm diameter containers. The temperature ranged from 24 to 34° Centigrade. The light level was natural outdoor light and there were no photoperiodic treatments or growth retardants used. Color determinations are in accordance with The Royal Horticultural Society Colour Chart 2001 edition, except where general color terms of ordinary dictionary significance are used. The growing requirements are similar to the species. 'Song of La Tigra' has not been tested under all possible conditions and phenotypic differences may be observed with variations in environmental, climatic, and cultural conditions, however, without any variance in genotype.

Botanical classification: *Dracaena reflexa lam.* 'Song of La Tigra'.

Parentage: 'Song of La Tigra' was discovered as a naturally occurring branch mutation of an unnamed cultivar of *Dracaena reflexa lam.*

Annual or perennial: Perennial.

Use: Ornamental.

Vigor: Moderate.

Growth habit: Upright.

Plant shape: Columnar.

Suitable container size: 15 cm. container.

Height: Average 62.6 cm. in height.

Width: Average 28.5 cm. in width.

Heat tolerance: Tolerant to 35° Centigrade.

Winter hardiness: USDA Zone 10.

Growth rate: Approximately 4 cm. per month.

Propagation: Terminal cuttings.

Time to initiate roots in summer: Approximately 21 days to produce roots on an initial cutting at 25–35° Centigrade.

Time to initiate roots in winter: Approximately 23 days to produce roots on an initial cutting at 23–32° Centigrade.

Time to produce a rooted cutting or liner in summer: Approximately 30 days at 25–35° Centigrade.

Time to produce a rooted cutting or liner in winter: Approximately 35 days at 23–32°.

Crop time: Approximately 7 months to produce a finished plant from a rooted cutting.

Root system: Fine and fibrous.

Stem:

*Basal branching.*—Present.

*Pinching.*—Required.

*Stem strength.*—Very strong.

*Stem color.*—137A to 137B, older stem 199D.

*Stem pubescence.*—Absent.

*Internode length.*—Average 1.0 cm.

*Stem shape.*—Rounded, dull.

*Stem surface.*—Smooth.

*Other characteristics.*—Leaf scars visible on older stems.

Foliage:

*Texture.*—Smooth, glossy, moderately leathery.

*Leaf arrangement.*—Alternate, spirally.

*Compound or single.*—Single.

*Quantity of leaves.*—Average 62.

*Leaf shape.*—Lorate.

*Leaf apex.*—Apiculate.

*Leaf base.*—Sheathing.

*Leaf length.*—Average 17.5 cm. in length.

*Leaf width.*—Average 2.6 cm. in width.

*Pubescence.*—Absent.

*Leaf margin.*—Entire, sinuate.

*Vein pattern.*—Parallel.

*Young leaf color (upper surface).*—Between 141A and 143A, base 145A to 145B.

*Young leaf color (lower surface).*—Between 141A and 143A, base 145A to 145B.

*Mature leaf color (upper surface).*—In between 139A and 147A, base 137A.

*Mature leaf color (lower surface).*—In between 137A and 147B, base 138A to 138B.

*Vein color.*—As leaf blade.

*Leaf attachment.*—Sessile.

*Durability of foliage to stress.*—High.

Flower: Flowering has not been observed.

Disease and pest resistance: 'Song of La Tigra' has not been observed for disease or pest resistance.

What is claimed is:

1. A new and distinct variety of *Dracaena* plant named 'Song of La Tigra' as described and illustrated.

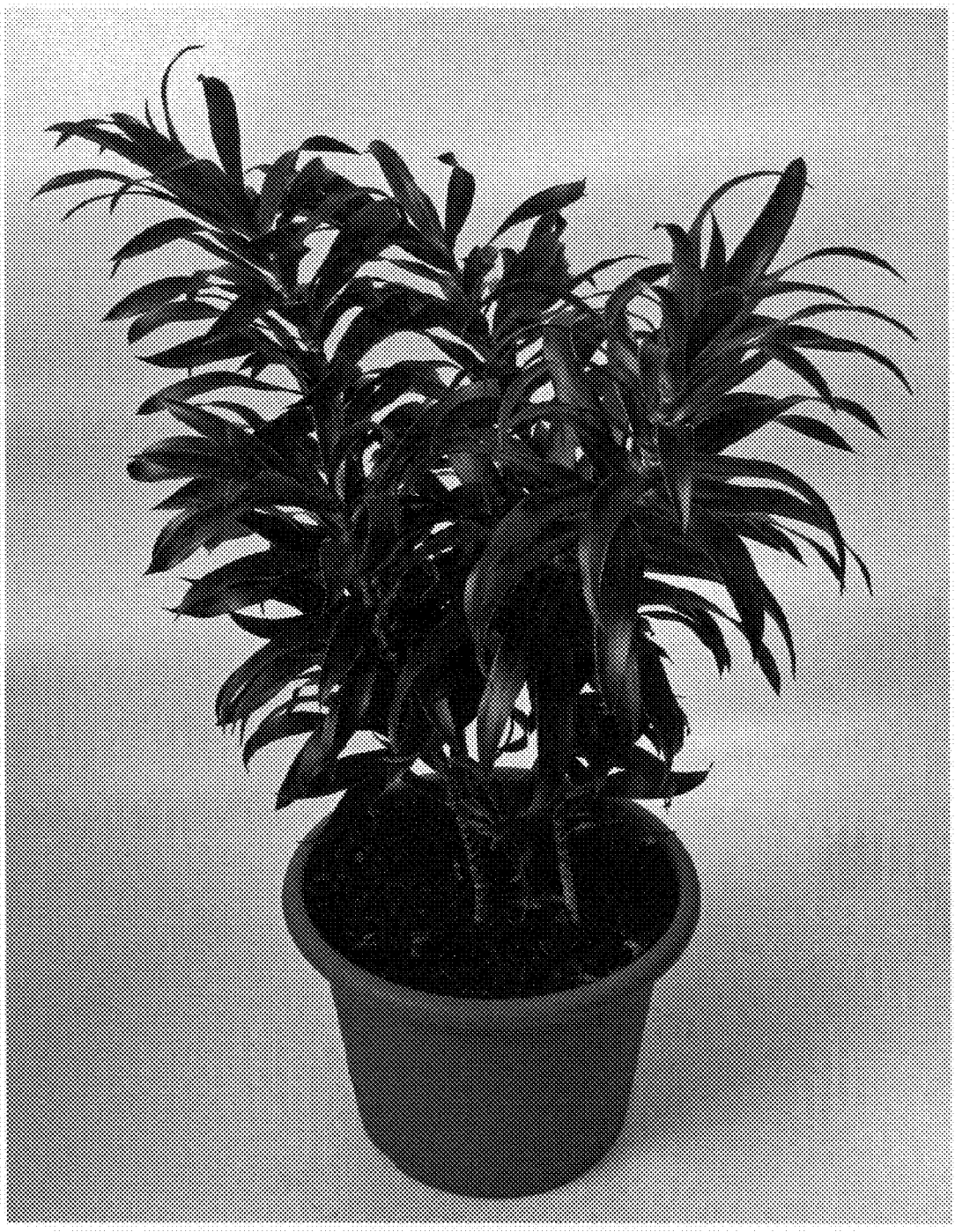

* * * * *